United States Patent [19]

Sala et al.

[11] Patent Number: 5,589,490
[45] Date of Patent: *Dec. 31, 1996

[54] BENZOIC ACID SUBSTITUTED DERIVATIVES HAVING CARDIOVASCULAR ACTIVITY

[75] Inventors: Alberto Sala; Aldo Banfi; Francesca Benedini; Roberta Cereda, all of Milan, Italy

[73] Assignee: Italfarmaco S.p.A., Milan, Italy

[ * ] Notice: The term of this patent shall not extend beyond the expiration date of Pat. No. 5,366,992.

[21] Appl. No.: 254,779

[22] Filed: Jun. 6, 1994

Related U.S. Application Data

[63] Continuation of Ser. No. 966,078, filed as PCT/EP91/01326, Jul. 15, 1991, Pat. No. 5,366,992.

[30] Foreign Application Priority Data

Jul. 26, 1990 [IT] Italy .................................. 21075 A/90

[51] Int. Cl.$^6$ .......................... A61K 31/21; C07C 203/04
[52] U.S. Cl. .......................... 514/330; 514/356; 514/365; 514/448; 514/466; 514/471; 514/409; 546/225; 546/322; 546/326; 548/201; 549/79; 549/441; 549/501; 558/482

[58] Field of Search ...................... 514/330, 356, 514/365, 448, 466, 471, 409; 546/225, 322, 326; 548/201; 549/79, 501, 441; 558/482

[56] References Cited

U.S. PATENT DOCUMENTS

| | | | |
|---|---|---|---|
| 4,200,640 | 4/1980 | Nagano | 558/482 |
| 5,049,694 | 9/1991 | Bron | 11/11 |
| 5,366,992 | 11/1994 | Sala | 514/409 |

*Primary Examiner*—Robert Gerstl
*Attorney, Agent, or Firm*—Oblon, Spivak, McClelland, Maier & Neustadt, P.C.

[57] ABSTRACT

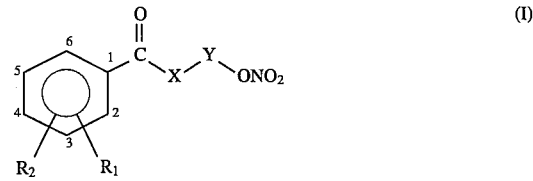

Compounds of formula (I) wherein X, Y, $R_1$ and $R_2$ have the meanings specified in the specification, are endowed with cardiovascular activity.

11 Claims, No Drawings

BENZOIC ACID SUBSTITUTED DERIVATIVES HAVING CARDIOVASCULAR ACTIVITY

This application is a continuation of application Ser. No. 07/966,078, filed Jan. 19, 1993, U.S. Pat. No. 5,366,992, which was filed as International Application No. PCT/EP91/01326 on Jul. 15, 1991.

The present invention relates to novel benzoic acid substituted derivatives of general formula (I)

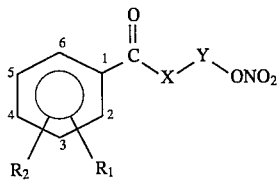

wherein:
X is an oxygen atom or the NH group;
Y is ethylene or a $C_3$–$C_6$ straight or branched alkylene, or a cyclopentylene, cyclohexylene or cycloheptylene group;
$R_1$ is the $OCOR_3$ group, wherein $R_3$ is methyl, ethyl or $C_3$–$C_5$ straight or branched alkyl, or the residue from a 5- or 6-membered monocyclic heterocycle which can be aromatic or partially or totally hydrogenated, containing one or more hetero-atoms selected independently from O, N and S;
$R_2$ is hydrogen, hydroxy, halogen, ($C_{1-4}$) alkyl, ($C_{1-4}$)alkoxyl, trifluoromethyl, sulfo, nitro, amino, or mono- or di-($C_{1-4}$) alkylamino;
$R_1$ and $R_2$, taken together, are the methylenedioxy group;
with the proviso that, when X is NH, Y is ethylene and $R_2$ is hydrogen, $R_1$ cannot be the $OCOR_3$ group at the 2-position in which $R_3$ is methyl;
and the pharmaceutically acceptable acid salts thereof.

Compounds having a substituted amido group with a $O_2NO$-alkylene chain are known in literature, including patent literature. For example, substances in which this group is bound to a heterocyclic aromatic ring are described in EP-A 300,400 and in U.S. Pat. No. 4,200,640. On the other hand, compounds in which said group is bound to a benzene ring are described in EP-A-83,256 and in Japanese published Patent application 54-81222.

In the compounds of formula I, Y is preferably ethylene or $C_{3-6}$ straight alkylene; $R_3$ is methyl, ethyl or a $C_3$–$C_6$ alkyl group or a heterocyclic group selected from 2-piperidinyl, 4-piperidinyl, 2-thienyl, 2-pyridyl, 3-pyridyl, 4-thiazolidinyl, 2-furyl; $R_2$ is hydrogen, halogen, nitro, methoxy or sulpho.

Preferred compounds of formula I are those wherein X is oxygen or NH, $R_1$ is acetoxy ($R_3$=methyl) or 4-thiazolidinylcarbonyloxy, Y and $R_2$ having the above defined meanings.

Particularly preferred compounds of formula I are those wherein X is oxygen or NH, $R_1$ is acetoxy, Y is ethylene, $R_2$ is hydrogen or halogen. $R_1$ is preferably in the 4- or 3-position.

Compounds of formula (I) can be obtained using the techniques described hereinbelow.

Thus, for instance, when compounds in which X is the NH group are desired, a molar amount of a benzoic acid of formula

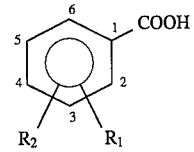

wherein $R_1$ and $R_2$ are as defined above, or of a functional reactive derivative thereof, such as an halide or an anhydride of either the same acid of formula (II) or mixed, is reacted with a substantially equimolecular amount of an aminoalkanol nitric ester, of formula $$H_2N-Y-ONO_2 \quad \text{III}$$

wherein Y is as defined above, or of a salt thereof, such as a halide or a nitrate.

The reaction is carried out in water or in an organic solvent, such as a halogenated aliphatic hydrocarbon, or in water/organic solvent mixtures, at a temperature ranging from 0° C. to room temperature and is complete within a time from about 1 hour to about 3 hours. When the compound of formula (III) is used in form of a salt thereof, the reaction is preferably carried out also in the presence of an organic or inorganic base. Generally a molar excess of an alkali or alkaline-earth metal carbonate or bicarbonate, or of a nitrogen organic base, such as trimethylamine, triethylamine, pyridine and the like, is used, said excess being calculated over the compound of formula (II).

Sometimes it can be more convenient to introduce the $NO_2$ group on the already formed amide of formula

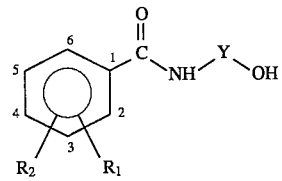

wherein $R_1$, $R_2$ and Y have the above mentioned meanings.

This procedure can advantageously be used instead of the above described one, when amides within formula (I), in which Y is a $C_{3-6}$ straight or branched alkylene or a cyclopentylene, cyclohexylene or cycloheptylene group, are desired.

In fact, corresponding nitric esters of the amino-alkanols to be condensed with the compound of formula (II) or with a functional derivative thereof, are slightly instable under the used reaction conditions, so that the final products are obtained in low yields or contaminated by undesired impurities.

According to this method, the starting benzoic acid of formula (II) is converted into a functional derivative thereof, for instance by reacting it with an alkyl-haloformate, to obtain a mixed anhydride. A molar amount of this anhydride is then treated with a substantially equivalent molar amount of an aminoalkanol of formula $$NH_2-Y-OH \quad V$$

wherein Y is as defined above, in an inert organic solvent, such as a ($C_{1-4}$) halogenated aliphatic hydrocarbon, at a temperature ranging from –5° C. to about 10° C. An amide of formula (IV) is obtained which can be either recovered and characterized, or used as such for the following steps. Thus, for instance, a molar amount of this substance can be reacted with a molar excess of trifluoromethanesulfonic anhydride and of a tetraalkylammonium nitrate, at a starting temperature from –60° to about –40° C. Even though the amounts of trifluoromethanesulfonic anhydride and tetraalkylammonium nitrate are not critical to the progress of the reaction, it is preferred to use about 2 or more molar equivalents of these reagents per mole of starting anhydride. It has also been noted that, when Y is cyclopentylene, cyclohexylene or cycloheptylene, substituting the hydroxy group with the ONO$_2$ group can involve an inversion in steric configuration.

The reaction can be carried out in a number of polar or apolar organic solvents. For example, $C_{1-4}$ halogenated aliphatic hydrocarbons, benzene, toluene, cyclohexane, dioxane, tetrahydrofurane, lower alkyl esters of lower aliphatic acids, di-($C_{1-4}$)alkyl esters, pyridine, dimethylsulfoxide, dimethylformamide, diethylacetamide, acetonitrile and mixtures thereof, can advantageously be used.

After about two hours, the reaction temperature is raised to about 25°–50° C. and kept for a time ranging from about 1 to about 4 hours, thereafter the reaction mixture is worked up according to the usual techniques.

The procedures described hereinbefore can advantageously be used also for the preparation of compounds of formula (I) in which Y, $R_1$ and $R_2$ are as defined above and X is an oxygen atom, by reaction, for example, a compound of formula (II), or a functional derivative thereof, with either the suitable mono-nitric ester of an α-ω-bis alkanol of formula

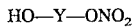
HO—Y—ONO$_2$         VI or the 1',ω-bis-alkanol itself, in which case the ONO$_2$ group is then introduced by means of the already described techniques.

Alternatively, the starting compound of formula (II), or a functional derivative thereof, can be reacted with a haloalkylamine or a haloalcohol of formula

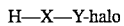
H—X—Y-halo         (VII)

wherein X and Y have the above mentioned meanings and halo is a halogen atom, to obtain compounds of formula

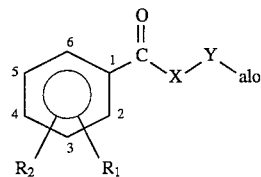
VIII wherein $R_1$ and $R_2$ have the above mentioned meanings, which compounds are then reacted with AgNO$_3$.

These reactions are effected in an inert organic solvent, such as a halogenated aliphatic hydrocarbon, at room temperature, using a slight molar excess of compound (VII) with respect to the starting benzoic acid (II), or a functional derivative thereof. Silver nitrate is used in equimolecular amounts about twofold those of compound (VIII) which can be either recovered and characterized, or used directly for the subsequent step.

Compounds of formula (I) wherein X is NH, Y and $R_2$ are as defined above and $R_1$ is a OCOR$_3$ group, in which $R_3$ is as defined above, and it can be at the 2-position when $R_2$ is hydrogen, Y is ethylene and $R_3$ is methyl, are in their turn suitable starting material for the preparation of other compounds according to the invention, falling within general formula (I).

Thus, if the OCOR$_3$ is subjected to hydrolysis, to obtain compounds of formula

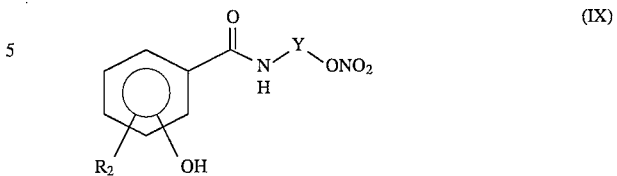
(IX)

wherein Y and $R_2$ have the above mentioned meanings, and the free hydroxyl of the resulting compound is acylated with an acid of formula

$R_3$—COOH         X wherein $R_3$ is as defined above, or with a functional derivative of said acid, such as a halide or a symmetrical or mixed anhydride, other substances of formula (I) can be prepared, in which the $R_3$ group, deriving from the acid of formula (X) or from a functional derivative thereof, is different from that of the starting product.

The compounds of formula (IX), as well as the pharmaceutically acceptable salts thereof, have cardiovascular activity and therefore are a further object of the present invention.

The procedure described above is used advantageously but not only, when compounds of formula (I) wherein $R_3$ is a residue from a heterocycle, are desired.

Whenever a

is present in the heterocyclic residue, compound (X) is preferably used in form of a functional derivative thereof, such as a mixed anhydride, said group optionally being protected previously by means of conventional protecting agents, such as bis-tert-butyl-dicarbonate, tert-butyl-dimethyl-silyl-chloride and the like.

As stated above, the compounds of the invention have cardiovascular activity. Particularly, they showed marked in vitro vasorelaxing activity and a remarkable antianginal activity in the test animal. Such favourable biological properties are associated to a negligeable hypotensive effect, whereas it is well known that one of the most severe side-effects of the nitro-derivatives already known and used in therapy is the onset of a marked postural hypotension, which in some cases can cause loss of consciousness, particularly if the patient remains in an erect position (Goodman and Gilman, The Pharmacological Bases of Therapeutics, 7$^{th}$ edition, page 813). Therefore, the compounds of the invention can be considered potential drugs having a specifically antianginal activity, which is another valuable feature, since angina attacks are often associated to more or less marked arrythmias.

The in vitro vasorelaxing activity of the compounds of the present invention was evaluated in the test of the noradrenaline-contracted rat aortha strip. The test was carried out according to the procedure described by K. Murakami et al., Eur. J. Pharmacol., 141, 195, 1987. The IC$_{50}$ values, i.e. the concentration of active substance, expressed in mol/l, inhibiting by 50% the aortha strip contraction, were evaluated.

The results obtained for some representative compounds of the invention are reported in the following Table 1.

TABLE 1

| Compound of Example | in vitro vasorelaxing activity $IC_{50}$ (mol/l) |
| --- | --- |
| 1 | $1.6 \times 10^{-7}$ |
| 2 | $2.3 \times 10^{-6}$ |
| 3 B | $1.2 \times 01^{-6}$ |
| 4 B | $1.1 \times 10^{-7}$ |
| 8 B | $1.3 \times 10^{-8}$ |
| 9 A | $1.6 \times 10^{-7}$ |
| 9 | $5.4 \times 10^{-7}$ |

In vivo antianginal activity was evaluated in Sprague Dawley anesthetized rats of 350–400 g mean weight, according to the procedure by M. Leitold et al., Arzneim. Forsch. 36, 1454, 1986. The test was carried out by intravenously administering to the animal one I.U./kg (equivalent to 3 mg/kg) of Arg-vasoprexine including a choronaric spasm which can be reproduced and electrocardiographically evidenced by an increase in the T wave. The compounds of the invention were administered through a gastric probe at a dose of 3 mg/kg, one hour before administering Arg-vasoprexine. The antianginal effect was expressed as percent inhibition of the increase in T wave versus controls.

The results obtained for some representative compounds of the invention are reported in Table 2.

TABLE 2

| Compound of Example | % Inhibition of the increase in T waves versus controls |
| --- | --- |
| 2 | 55 |
| 4 B | 53 |
| 8 B | 61 |
| 9 A | 42 |

The hypotensive effect was evaluated in the anesthetized rat. Male Sprague Dawle rats, weighing 350–400 g, anesthetized with urethane (1.25 g/kg i.p.) were used. Arterial pressure was monitored by means of a catheter inserted in left carotide, in its turn connected with a pressure transducer. The compounds of the invention were administered in bolus, in the femoral vein, at increasing doses and the hypotensive effect was evaluated as the percent reduction in mean arterial pressure compared with basal values. Thereafter, the relative potency of the compounds of the invention was measured as $ED_{20}$, i.e. the amount reducing pressure by 20%.

Tests effected on representative compounds of the invention proved that the $ED_{20}$ were higher than 0.5 mg/kg body weight.

Moreover, such favourable biological properties are associated with a low toxicity: in fact the $LD_{50}$ values, determined according to the method by Lichtfield and Wilcoson, J. Pharm. Expt. Ther. 96, 99, 1949, were higher than 500 mg/kg i.p.

The present invention also relates to the use of the novel compounds of the invention as antianginal agents, as well as to all of the acts and aspects which can industrially apply to said use, including the incorporation of said compounds in pharmaceutical compositions. Examples of said pharmaceutical compositions are tablets, dragees, syrups and vials, the latter suitable for both the oral and the intramuscular or intravenous administrations. Said compositions will contain the active ingredient alone or in admixture with the usual pharmaceutically acceptable excipients and carriers.

The doses of the active ingredient for the cure of the anginal attacks can range within wide limits, depending on the nature of the used compound. The preferred dosage forms generally contain from about 1 to about 10 mg of the active ingredient, and they are suitable for administration one or more times daily.

The compounds used as the starting material in the following Examples are commercial products, or they can be prepared according to the literature: in this instance, the related references are reported hereinbelow.

a) 2-Nitrooxyethylamine nitrate—Bull. Soc. Chem. Fr., 11, 470, 1944.

b) 3-Acetoxy and 4-acetoxy-benzoic and 3-acetoxy-benzoic acid chlorides—Arzneim. Forsch. 14, (4), 324, 1964.

c) 2-Acetoxy-4-chloro-benzoic acid—JACS, 89, 4853, 1967.

d) 2-Propionyloxy-benzoic acid—J. Biol. Chem., 255, 2816, 1980.

e) 3-(Tert.-butoxycarbonyl)-4-thiazolidinyl-carboxylic acid—JACS, 87, 620, 1965.

$^1$H-NMR Spectra were carried out in dimethylsulfoxide (DMSO) with a VARIAN GEMINI 200 spectrometer. $^{13}$H-NMR Spectra were performed using a VARIAN GEMINI 200 Spectrometer, taking the dimethylsulfoxide peak at 39.5 p.p.m. as the reference.

The invention is further illustrated by the following examples.

EXAMPLE 1

3-Acetoxy-N-(2-nitroxyethyl)-benzamide 18.6 g (0.110 mole) of 2-nitroxy-ethylamine nitrate at 0° C. were added to a solution of 40.7 g (0.458 mole) of sodium bicarbonate in 140 ml of water and 120 ml of chloroform. After stirring for 10 min, 22.5 g (0.113 mole) of 3-acetoxybenzoic acid chloride were dropped therein and the resulting mixture was stirred for one hour at 0° C. The reaction mixture was warmed to room temperature, the two phases were separated and the organic phase was washed with water and dried over sodium sulfate. The crude title product was obtained, which was recrystallized from ethyl ether. M.p. 89°–91° C. Yield 26.5 g.

EXAMPLE 2

4-Acetoxy-N-(2-nitroxyethyl)-benzamide

Starting from 0.113 mole of 4-acetoxybenzoic acid chloride and 0.110 mole of 2-nitrooxy-ethylamine nitrate, and operating substantially as described in the preceding Example, 22 g of the title compound were obtained. M.p. 95°–97° C. (ethyl ether).

EXAMPLE 3

3-Acetoxy-N-(5-nitroxypentyl)-benzamide

A—3-Acetoxy-N-(5-hydroxypentyl)-benzamide—10.5 ml.

(0.111 mole) of ethyl chloroformate were added at 0° C., under stirring, to a solution of 20 g (0.111 mole) of 3-acetoxybenzoic acid in 500 ml of chloroform and 15.3 ml of triethylamine. After one hour at 0° C., a solution of 11.4 g (0.111 mole) of 5-amino-1-pentanol was added and the resulting reaction mixture was stirred for 4 hours, then it was washed with water and the separated organic phase was dried over sodium sulfate. 31.8 g of the crude product were obtained, which was purified on a silica gel column, eluting with 91/9 (v/v) ethyl acetate/n-hexane. 7.5 g of the title product were recovered in form of an oil.

B—3-Acetoxy-N-(5-nitroxypentyl)-benzamide 10.6 g (0.0377 mole) of trifluoromethanesulfonic anhydride were dropped into a solution of 5 g (0.0188 mole) of the compound prepared in A) and 11.5 g (0.0377 mole) of tetrabutylammonium nitrate in 500 ml of methylene chloride, 3.08 ml of pyridine and 37.5 ml of N,N-dimethylformamide cooled to −50° C. The reaction mixture was heated to 40° C. and kept at this temperature for 3 hours, then it was washed with water, 0.5% aqueous hydrochloric acid, 5% aqueous sodium bicarbonate, then again with water, finally dried over sodium sulfate. After evaporating the solvent, a crude product was obtained which was purified on a silica gel column. Yield: 4 g of the title compound, in form of an oil, having the following characteristics:

| i) Elemental analysis: | % C | % H | % N |
|---|---|---|---|
| Calculated | 54.19 | 5.85 | 9.03 |
| Found | 54.01 | 5.92 | 8.98 | ii) $^1$H-NMR (in DMSO): characteristic resonance peaks were evidenced at the following δ(p.p.m.): 8.54 (t, 1H); 7.74 (dd, 1H); 7.59 (t, 1H); 7.51 (t, 1H); 7.29 (dd, 1H); 4.52 (t, 2H); 3.26 (q, 2H); 1.77–1.29 (m, 6H)

iii) $^{13}$C-NMR (in DMSO): characteristic resonance peaks were evidenced at the following δ(p.p.m.): 169.55; 165.44; 150.69; 156.36; 129.67; 124.81; 124.72; 120.89; 73.87; 38.91; 28.47; 25.70; 22.52; 20.72.

EXAMPLE 4

2-Acetoxy-N-(5-nitroxypentyl)-benzamide

A—2-Acetoxy-N-(5-hydroxypentyl)-benzamide

The compound was prepared as described in Example 3A, starting from 10 g (0.0555 mole) of acetylsalicylic acid. 5.7 of a product were obtained, in form of an oil, which was directly used in the subsequent step.

B—2-Acetoxy-N-(5-nitroxyethyl)-benzamide

The title compound was obtained substantially as described in Example 3G. Yield: 3.2 g of a pure product having the following characteristics:

| i) Elemental analysis: | % C | % H | % N |
|---|---|---|---|
| Calculated | 54.19 | 5.85 | |
| Found | 54.35 | 5.88 | 9.04 | ii) $^1$H-NMR (in DMSO): characteristic resonance peaks were evidenced at the following δ(p.p.m.): 8.29 (t, 1H); 7.58–7.46 (m, 2H); 7.33 (t, 1H); 7.18 (d, 1H); 4.53 (t, 2H); 3.20 (q, 2H); 2.21 (s, 3H); 1.77–1.29 (m, 6H)

iii) $^{13}$C-NMR (in DMSO): characteristic resonance peaks were evidenced at the following δ(p.p.m.): 169.15; 165.56; 148.19; 131.25; 129.89; 129.05; 125.96; 123.40; 73.88; 38.53; 28.44; 25.66; 22.41; 20.66.

EXAMPLE 5

2-Acetoxy-N-(cis-2-nitroxycyclohexyl)-benzamide

A—2-Acetoxy-N-(trans-2-hydroxycyclohexyl)-benzamide

Prepared substantially according to the procedure described in Example 3A, starting from 5 g (0.033 mole) of trans-2-hydroxy-cyclohexylamine hydrochloride and 5.9 g (0.33 mole) of acetylsalicylic acid. 2.6 g of the product were obtained, which was used directly in the subsequent step.

B—2-Acetoxy-N-(cis-2-nitroxycyclohexyl)-benzamide

Prepared according to the procedure described in Example 3B. 1 g of the title compound was obtained. M.p. 143°–145° C. (chloroform/acetone=9/1).

EXAMPLE 6

2-Acetoxy-4-chloro-N-(2-nitroxyethyl)-benzamide

Into a solution of 10 g (0.0466 mole) of 2-acetoxy-4-benzoic acid and 6.5 ml (0.0466 mole) of triethylamine in 250 ml of chloroform, cooled to 5° C. were dropped first 4.4 ml (0.0466 mole) of ethyl chloroformate then, one hour later, a solution of 7.9 g (0.0466 mole) of 2-nitroxy-ethylamine nitrate and 6.5 ml (0.0466 mole) of triethylamine in 50 ml of chloroform. The reaction mixture was kept at 0° C. under stirring, then washed with 300 ml of water, then with 300 ml of 5% aqueous sodium bicarbonate, dried over sodium sulfate and concentrated. The resulting residue was chromatographed on a silica gel column, eluting with methylene chloride/acetone=92/8 (v/v), 6.5 g of the title product were obtained. M.p. 75°–77° C. (n-hexane).

EXAMPLE 7

N-2-(Nitroxyethyl)-2-propionyloxy-benzamide

The title compound was prepared according to the procedure described in the preceding Example, starting from 5 g (0.0258 mole) of 2-propionyloxy-benzoic acid and 4.4 g (0.0258 mole) of 2-nitrooxyethylamine nitrate. The residue resulting from the working up of the reaction mixture was chromatographed on a silica gel column, eluting with methylene chloride/acetone=95/5 (v/v). 4.5 g of the product were obtained, in form of an oil, having the following characteristics:

| i) Elemental analysis: | % C | % H | % N |
|---|---|---|---|
| Calculated | 51.06 | 5.00 | 9.92 |
| Found | 51.1 | 4.97 | 9.89 | ii) $^1$H-NMR (in DMSO): characteristic resonance peaks were evidenced at the following δ(p.p.m.): 8.52 (t, 1); 7.59–7.46 (m, 2H); 7.33 (t, 1H); 7.18 (d, 1H); 4.59 (t, 2H); 3.53 (q, 2H); 2.55 (q, 2H); 1.10 (t, 3H)

iii) ⁻C-NMR (in DMSO): characteristic resonance peaks were evidenced at the following δ(p.p.m.): 172.20; 166.16; 147.70; 131.97; 129.41; 127.81; 124.72; 122.15; 72.33; 36.60; 28.50; 9.30.

EXAMPLE 8

2-Acetoxy-2-nitroxyethylbenzoate

A—2-Acetoxy-2-bromoethylbenzoate 5.6 ml (0.0755 mole) of 2-bromoethanol were added to a solution of 10 g (0.0504 mole) of 2-acetoxy-benzoyl chloride and 13.6 ml (0.1 mole) of triethylamine in 200 ml of methylene chloride. The reaction mixture was kept at room temperature for 2.5 hours; when it was washed with water, the organic phases were separated and the organic phase was dried over sodium sulfate. The product was purified on a silica gel column, eluting with n-hexane/ethyl acetate=75/25

(v/v) to obtain 3 g of the product, in the form of an oil, which was used directly in the subsequent step.

B—2-Acetoxy-2-nitroxyethylbenzoate

The product in step A (0.0105 mole) was dissolved in 15 ml of acetonitrile and a solution of 4.08 g (0.024 mole) of silver nitrate in 28 ml of acetonitrile was added thereto. The resulting mixture was refluxed for 4 hours, shielded from light, then the formed salts were filtered and the solvent was evaporated off. The resulting residue was taken up into methylene chloride, washed with water, the organic phase was recovered, dried over sodium sulfate and concentrated to give a residue which was purified on a silica gel column, eluting with n-hexane/ethyl acetate=55/45 (v/v). 2 g of the title compound were obtained, having the following characteristics:

| i) Elemental analysis: | % C | % H | % N |
|---|---|---|---|
| Calculated | 49.08 | 4.12 | 5.20 |
| Found | 49.18 | 4.16 | 5.16 | ii) $^1$H-NMR (in DMSO): characteristic resonance peaks were evidenced at the following δ(p.p.m.): 7.96 (dd, 1H); 7.71 (dt, 1H); 7.43 (t, 1H); 7.26 (d, 1H); 4.86 (m, 2H); 4.56 (m, 2H); 2.29 (s, 3H);

iii) $^{13}$C-NMR (in DMSO): characteristic resonance peaks were evidenced at the following δ(p.p.m.): 164.16; 150.36; 134.84; 131.58; 126.57; 124.34; 122.87; 71.55; 61.13; 20.58.

EXAMPLE 9

N-(2-Nitroxyethyl)-2-[(4-thiazolidinyl)carbonyloxy]-benzamide hydrochloride

A—2-Hydroxy-N-(2-nitroxyethyl)-benzamide 13 g (0.0485 mole) of 2-acetoxy-N-2-(nitrooxyethyl)-benzamide (prepared as described in Japanese published patent application No 54-81222) and 1 g (0.0147 mole) of imidazole were dissolved in 223 ml of methanol and 44 ml of water, and the resulting solution was stirred at room temperature for 12 hours. Solvent was evaporated off and the resulting residue was taken up into methylene chloride and washed with water. The organic phase was separated, dried over sodium sulfate and evaporated to dryness under reduced pressure. The resulting residue was purified on a silica gel column, eluting with soluene/methanol=97/3 (v/v). 4.5 g of a product were obtained. M.p. 76°–78° C. (n-hexane).

B—2-{[(3-tert.-butoxycarbonyl)-4-thiazolidinyl]carbonyloxy}-N-(2-nitroxyethyl)-benzamide To 6.2 g (0.0265 mole) of 3-(tert-butoxycarbonyl)-4-thiazolidinecarboxylic acid and 3.67 ml (0.0265 mole) of triethylamine in 50 ml of chloroform were added, at 0° C. 2.53 ml (0.0265 mole) of ethyl chloroformate and, after one hour, 6 g (0.0265 mole of the compound prepared in step A. After that, the reaction mixture was stirred at room temperature for 12 hours, the organic phase was washed with water, separated, dried over sodium sulfate and concentrated under reduced pressure. The residue was purified on silica gel, eluting with chloroform/methanol=97/3 (v/v). 3.6 g of the product were obtained, which was used directly in the subsequent step.

C—N-(2-Nitroxyethyl)-2-[(4-thiazolindinyl)carbonyloxy]-benzamide

The compound obtained in step B (3.5 g, 0.00802 mole) was dissolved in 20 ml of ethyl acetate and this solution was added with 30 ml of a 2.76M solution of hydrochloric acid in ethyl acetate. The resulting mixture was left to stand for 1 hour, to obtain a precipitate which was recovered by filtration, washed with ethyl acetate and dried. Yield: 2.3 g. M.p.=164°–166° C. (ethyl acetate).

EXAMPLE 10

2-Nicotincyloxy-N-(2-nitroxyethyl)-benzamide

To a solution of 2.7 g (0.02211 mole) of nicotinic acid and 3.1 ml (0.0221 mole) of triethylamine in 20 ml of chloroform, kept at 0° C. 2,1 ml (0.0221 mole) of ethyl chloroformate and, after one hour, 5 g (0.0221 mole) of the compound of Example 9A, were added. The mixture was kept at room temperature for 20 hours, the organic phase was washed with water, separated, dried over sodium sulfate and concentrated under reduced pressure. The obtained residue was purified on a silica gel column, eluting with ethyl acetate/n-hexane=70/30 (v/v). M.p. 94°–96° C.

EXAMPLE 11

2-Acetoxy-5-nitroxypentylbenzoate

A—2-Acetoxy-5-bromopentylbenzoate

2-Acetoxy-5-bromopenthylbenzoate was prepared according to the procedure described in Example 8A, starting from 4.75 g (0.024 moles) 2-acetoxybenzoyl ·chloride and 6 g (0.036 moles) 5-bromoethanol. 3.5 g product, which was used directly in the subsequent step, were obtained.

B—2-Acetoxy-5-nitroxypentylbenzoate

The title compound was prepared according to the procedure of Example 8B. The desired product (3 g), in the form of an oil, were obtained with the following characteristics:

| i) Elemental analysis: | % C | % H | % N |
|---|---|---|---|
| Calculated | 54.02 | 5.50 | 4.50 |
| Founded | 54.01 | 5.47 | 4.46 | ii) $^1$H-NMR (in DMSO): characteristic resonance peaks were evidenced at the following δ(p.p.m.): 7.96 (dd, 1H); 7.70 (dt, 1H); 7.43 (t, 1H); 7.26 (t, 1H); 4.55 (t, 2H); 4.25 (t, 2H); 2.24 (s, 3H); 1.82–1.65 (m, 4H); 1.55–1.37 (m, 3H).

iii) $^{13}$C-NMR (in DMSO): characteristic resonance peaks were evidenced at the following δ(p.p.m): 169.35; 164.33; 150.24; 134.47; 131.42; 126.53; 124.29; 123.52; 73.93; 64.86; 27.89; 25.94; 21.94; 21.01.

Following substantially the same procedure described in the above Examples, starting from the appropriate compounds of formula (II) and formula (IX), the following compounds of formula (I) can be prepared:
2-Acetoxy-3-bromo-N-(2-nitroxyethyl)-benzamide
2-Acetoxy-4-diethylamine-N-(2-nitroxyethyl)-benzamide
N-(2-Nitroxyethyl)-2-pentanoyloxy-benzamide
2-Nicotinoyloxy-2-nitroxyethylbenzoate
3-Nicotinoyloxy-2-nitroxyethylbenzoate
3-Nicotinoyloxy-N-(2-nitroxyethyl)-benzamide
2-Acetoxy-3-nitro-N-(2-nitroxyethyl)-benzamide
3-Nitro-N-(2-nitroxyethyl)-2-propionyloxy-benzamide
3-Nitro-N-(2-nitroxypentyl)-2-propionyloxy-benzamide 2-Acetoxy-3-nitro-2-nitroxyethylbenzoate
2-Nicotinoyloxy-N-(5-nitroxypentyl)-benzamide
3-Nicotincyloxy-N-(5-nitroxypentyl)-benzamide
2-Nicotinoyloxy-5-nitroxypentylbenzoate
2-Acetoxy-5-chloro-N-(2-nitroxyethyl)-benzamide
2-Acetoxy-N-(2-nitroxyethyl)-4-trifluoromethyl-benzamide
2-Acetoxy-N-(5-nitroxypentyl)-4-trifluoromethyl-benzamide
2-Acetoxy-5-fluoro-N-(2-nitroxyethyl)-benzamide
5-Fluoro-3-propionyloxy-2-nitroxyethylbenzoate
N-(2-Nitroxypropyl)-4-propionyloxy-benzamide
2-Acetoxy-4-methoxy-N-(2-nitroxyethyl)-benzamide
2-Acetoxy-4-methoxy-N-(2-nitroxyhexyl)-benzamide
2-Acetoxy-5-methyl[2,2-dimethyl-3-nitroxy)propyl]-benzoate
2-Acetoxy-5-methoxy-2-nitroxypropylbenzoate
3-Acetoxy-5-sulpho-2-nitroxyethylbenzoate
N-(2-Nitroxyethyl)-2-thenoyloxy-benzamide
N-(2-Nitroxypropyl)-2-(2-furoyloxy)-benzamide
N-(2-Nitroxyethyl)-2-(2-piperidinylcarbonyloxy)-benzamide
3-Nitro-(2-nitroxypropyl)-2-(2-piperidinylcarbonyloxy)-benzamide
2-Thenoyloxy-2-nitroxyethylbenzoate
2-Thenoyloxy-2-nitroxybutylbenzoate
2-(2-Piperidinylcarbonyloxy)-2-nitroxyethylbenzoate
N-(2-Nitroxyethyl)-4-(4-piperidinylcarbonyloxy)benzamide
3,4-Methylenedioxy-N-(2-nitroxyethyl)-benzamide

We claim:
1. A compound of the formula I

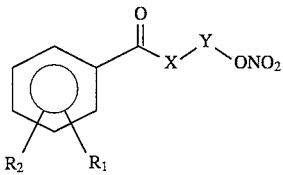

wherein:
X is the NH group;
Y is an ethylene or a $C_3$–$C_6$ straight or branched alkylene, or a cyclopentylene, cyclohexylene or cycloheptylene group;
$R_1$ is the $OCOR_3$ group, wherein $R_3$ is methyl, ethyl or $C_3$–$C_5$ straight or branched alkyl, or the residue from a 5- or 6-membered monocyclic heterocycle which can be aromatic or partially or totally hydrogenated, containing one or more hetero-atoms selected independently from O, N and S;
$R_2$ is hydrogen, hydroxy, halogen, $C_{1-4}$ alkyl, $C_{1-4}$ alkoxy, trifluoromethyl, sulfo, nitro, amino, or mono- or di- $C_{1-4}$ alkylamino; or
$R_1$ and $R_2$, taken together, are the methylenedioxy group;
with the proviso that when Y is ethylene and $R_2$ is hydrogen, $R_1$ cannot be the $OCOR_3$ group at the 2-position in which $R_3$ is methyl;
and the pharmaceutically acceptable acid salts thereof.
2. The compound of claim 1, wherein
Y is ethylene or $C_{3-6}$ straight alkylene;
$R_3$ is methyl, ethyl or a $C_{3-6}$ alkyl group or a heterocyclic group selected from 2-piperidinyl, 4-piperidinyl, 2-thienyl, 2-pyridyl, 3-pyridyl, 4-thiazolidinyl, 2-furyl; and $R_2$ is hydrogen, halogen, nitro, methoxy or sulfo.
3. The compound of claim 1 wherein $R_1$ is methyl or 4-thiazolidinylcarbonyloxy.
4. The compound of claim 1, wherein
$R_3$ is methyl;
Y is ethylene; and
$R_2$ is hydrogen or halogen.
5. The compound selected from the group consisting of 4-acetoxy-N-(2-nitroxyethyl)-benzamide and N-(2-nitroxyethyl)-2-[4-thiazolidinyl)carboxyloxy]-benzamide hydrochloride.
6. A pharmaceutical composition comprising as the active principle, a pharmaceutically effective amount of the compound of claim 1 in admixture with a pharmaceutically acceptable excipient.
7. A compound of the formula I

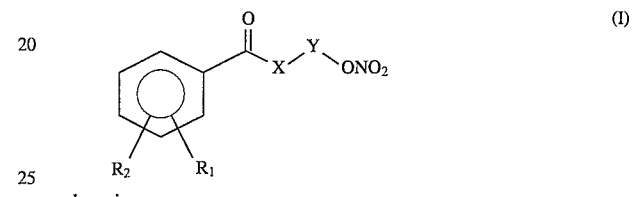

wherein
X is an oxygen atom;
Y is an ethylene or a $C_3$–$C_6$ straight or branched alkylene, or a cyclopentylene, cyclohexylene or cycloheptylene group;
$R_1$ is the $OCOR_3$ group, wherein $R_3$ is methyl, ethyl or $C_3$–$C_5$ straight or branched alkyl or the residue from a 5- or 6-membered monocyclic heterocycle which can be aromatic or partially or totally hydrogenated, containing one or more hetero-atoms selected independently from O, N and S;
$R_2$ is hydrogen, hydroxy, halogen, $C_{1-4}$ alkyl, $C_{1-4}$ alkoxy, trifluoromethyl, sulfo, nitro, amino, mono- or di- $C_{1-4}$ alkylamino; or
$R_1$ and $R_2$, taken together, are the methylenedioxy group;
and the pharmaceutically acceptable acid salts thereof.
8. The compound of claim 7, wherein
Y is ethylene or $C_{3-6}$ straight alkylene;
$R_3$ is methyl, ethyl or a $C_{3-6}$ alkyl group or a heterocyclic group selected from 2-piperidinyl, 4-piperidinyl, 2-thienyl, 2-pyridyl, 3-pyridyl, 4-thiazolidinyl, 2-furyl; and
$R_2$ is hydrogen, halogen, nitro, methoxy or sulfo.
9. The compound of claim 7, wherein
$R_3$ is methyl or 4-thiazolidinylcarbonyloxy.
10. The compound of claim 7, wherein
$R_3$ is methyl;
Y is ethylene; and
$R_2$ is hydrogen or halogen.
11. A pharmaceutical composition comprising as the active principle, a pharmaceutically effective amount of the compound of claim 7 in admixture with a pharmaceutically acceptable excipient.

* * * * *